United States Patent [19]

Lehmann et al.

[11] Patent Number: 4,705,695

[45] Date of Patent: Nov. 10, 1987

[54] METHOD FOR COATING PHARMACEUTICAL FORMULATIONS

[75] Inventors: Klaus Lehmann, Rossdorf; Dieter Dreher, Darmstadt; Harry Goetz, Alsbach-Haehnlein, all of Fed. Rep. of Germany

[73] Assignee: Röhm GmbH Chemische Fabrik, Darmstadt, Fed. Rep. of Germany

[21] Appl. No.: 744,330

[22] Filed: Jun. 13, 1985

[30] Foreign Application Priority Data

Jun. 13, 1984 [DE] Fed. Rep. of Germany ....... 3421860
Jul. 19, 1984 [DE] Fed. Rep. of Germany ....... 3426587

[51] Int. Cl.$^4$ .............................................. A61K 9/32
[52] U.S. Cl. ......................................... 427/3; 424/33; 424/19
[58] Field of Search ........................ 424/33, 19; 427/3

[56] References Cited

U.S. PATENT DOCUMENTS

| | | | |
|---|---|---|---|
| 3,919,436 | 11/1975 | Takele | 427/3 |
| 4,017,647 | 4/1977 | Ohmo | 427/3 |
| 4,088,798 | 5/1978 | Michaelis | 427/3 |
| 4,452,862 | 6/1984 | Markert | 424/33 |

FOREIGN PATENT DOCUMENTS

| | | |
|---|---|---|
| 00764 | 1/1982 | European Pat. Off. . |
| 0058765 | 9/1982 | European Pat. Off. . |
| 68189 | 5/1983 | European Pat. Off. . |
| 2614662 | 1/1977 | Fed. Rep. of Germany . |
| 2712043 | 9/1977 | Fed. Rep. of Germany . |
| 2813634 | 10/1978 | Fed. Rep. of Germany . |
| 3049179 | 7/1982 | Fed. Rep. of Germany . |

OTHER PUBLICATIONS

Academy of Pharmaceutical Sciences Jackson, Midwest Regional Meeting 5/17/1976.

*Primary Examiner*—Sam Sibierbeg
*Attorney, Agent, or Firm*—Oblon, Fisher, Spivak, McClelland, & Maier

[57] ABSTRACT

A method for coating solid pharmaceutical formulations, comprising coating said solid formulation with an aqueous fluid, film forming coating medium comprising a dissolved polymer prepared from acrylic and/or methacrylic monomers having a side group containing a tertiary amine substituent, wherein the amine nitrogen atom is converted to the ammonium salt form; and then drying said coated film.

7 Claims, No Drawings

METHOD FOR COATING PHARMACEUTICAL FORMULATIONS

BACKGROUND OF THE INVENTION

1. Field of the Invention

The invention relates to a method for coating solid pharmaceutical formulations by applying to said formulations a film comprised of a film-forming coating medium in the fluid state, the liquid phase of which medium is comprised primarily of water, and then drying the film. (The term "pharmaceutical formulations" should be understood to mean not only tablets, capsules, and dragees, but also pellets, globules, granules, crystals, and similarly compacted or agglomerated medicinal particles.)

2. Description of the Background

Aqueous coating media for solid pharmaceutical formulations have been in general use for a long time. A classical method for employing an aqueous coating is to coat a solid formulation with sugar solutions. Today this technique has been substantially replaced by other methods of film coating, i.e., "film drageeing". These film coating methods employ aqueous coating media comprising water-soluble cellulose derivatives, polyethylene glycols, polyvinyl alcohol, or polyvinyl pyrrolidone as binders or binder adjuvants, or organic coating media solutions.

Aqueous coating media have the advantage of being non-flammable, with non-explosive vapors, and the process of evaporating the water from the coating has no adverse effect on the environment. However, the water-soluble binders employed in known aqueous coating media are not entirely satisfactory. To the extent the coatings contain cellulose derivates as a binder, they are subject to attack by microorganisms, particularly at high humidity and temperature conditions, e.g. in tropical climates. Present aqueous coating solutions are often difficult to color, and require a high binder-to-pigment ratio. The dried films applied to solid pharmaceutical formulations result in coatings which are insufficiently glossy, have inadequate resistance to abrasion, and have poor storage stability. They are hygroscopic to some extent, and under high humidity tend to become adhesive, so that, e.g., the coated formulations may stick together.

A proven non-water-based coating medium comprises alcoholic solutions of acrylic and/or methacrylic polymers having side groups containing tertiary amino groups (Ger. Pat. No. 1,090,381). On solid pharmaceutical formulations these coating media produce smooth, shiny coatings which are non-hygroscopic and are not susceptible to microorganisms. In the acid medium of gastric juice the tertiary amino groups are converted to the salt form, in which form the polymers are readily water-soluble, so that the coating dissolves in the stomach in a few minutes. The sole disadvantage of this well-tried and tested coating medium is the fact that it contains flammable solvents, which must be recovered from the air outlet of the coating apparatus for reasons of safety and for the prevention of air pollution.

A water soluble binder has been sought for the preparation of aqueous coating media, which binder is superior to the known water-soluble binders in that aqueous solutions containing the binder can be highly colored if desired, and even when highly colored, said solution yields a coating with high gloss. Further, the binder sought should be superior in that a coating containing the binder on solid pharmaceutical formulations should be abrasion resistant, relatively non-brittle and non-hygroscopic, and not subject to microbiological attack. In addition, the resulting coating should be free from disagreeable tastes and odors, and of course should be nontoxic.

SUMMARY OF THE INVENTION

Accordingly, one object of the present invention is to provide an aqueous coating medium for solid pharmaceutical formulations which contains a binder of superior binding properties.

Another object of the invention is to provide a coating for solid pharmaceutical formulations which is abrasion resistant, relatively non-brittle and non-hygroscopic and not subject to microbiological attack.

Still another object of the invention is to provide a coating for solid pharmaceutical formulations which is free from disagreeable tastes and odors and which is nontoxic.

Briefly, these objects and other objects of the present invention as hereinafter will become more readily apparent can be attained by a method for coating solid pharmaceutical formulations by coating the solid formulation with an aqueous fluid, film forming coating medium comprising a dissolved polymer prepared from acrylic and/or methacrylic monomers having a side group containing a tertiary amine substituent, wherein the amine nitrogen atom is converted to the ammonium salt form and then drying the coated film.

DETAILED DESCRIPTION OF THE PREFERRED EMBODIMENTS

The term "coating medium", as used in the present invention, designates a liquid, film-forming medium which is used for coating solid pharmaceutical formulations, such that a solid coating is produced on the pharmaceutical formulation when the film is dried.

In the simplest case, the present coating medium is comprised solely of a liquid solvent component with a binder dissolved therein. In most cases, however, the said medium will further be comprised of pigments, fillers, and softening agents (plasticizers), and other excipients such as flavorants, active ingredients, gloss agents, and lubricants (or dispersants). A special embodiment of such coating media comprises, in addition to the binder dissolved in the liquid component, a dispersed film-forming binder which is insoluble in the liquid component.

The said liquid component is comprised primarily of water, i.e., greater than 80 wt. % water, preferably 90 to 100 wt. % water. In addition, water-miscible adjuvants may be employed along with water, which adjuvants serve as solvent enhancers, softeners (plasticizers), or film-forming aids and are nonfluid or semifluid under the usual drying conditions. Examples of such adjuvants include ethylene glycol, ethylene glycol monomethyl ether, propylene glycol, diethylene glycol, polyethylene glycol, glycerine, glyceryl triester(s), and citric acid ester(s). Coating media for pharmaceutical formulations generally contain substantial amounts of pigments and/or fillers. The binder of the present invention is distinguished by excellent binding to pigments. A product with up to 3 parts pigment per 1 part binder by wt. can be employed. Ordinarily this ratio is in the range of 1:1 to 2:1. The generally used pigments and fillers are employed in the present coating media.

The coating medium must be film-forming. That is, when it is applied to the surface of a solid pharmaceutical formulation it must be capable of forming an coherent, uniform film thereon. The viscosity of the coating medium should be in the range of 20 to 50 mPa-sec as measured by a rotary viscometer.

Typical coating media according to the present invention are comprised of the liquid component in the amount of 60-90 wt. %, the binder in the amount of 5-15 wt. %, which binder is soluble in said liquid component, optionally an undissolved, dispersed film-forming binder in the amount of up to 30 wt. %, and pigments and fillers in the amount of up to 25 wt. %.

The Dissolved Binder

The binder is a polymer produced primarily from acrylic and/or methacrylic monomers. The monomers contain a $CH_2=CH-CO-$ or a $CH_2=C(CH_3)-CO-$ group and represent at least 50 wt. %, preferably 80-100 wt. %, of the polymer. Comonomers which may be used which do not belong to the group of the acrylic and methacrylic monomers include vinyl esters such as vinyl acetate, vinyl propionate and vinyl butyrate, vinylpyrrolidone, maleic acid, fumaric acid, itaconic acid; the half and full esters of maleic, fumaric, and itaconic acids; styrene, vinyltoluene, and vinyl ether.

A characteristic feature of the polymer is that it has side groups each of which contains a salt of a tertiary amino group, which salts classically are produced by a salt forming reaction of the tertiary amino group with one equivalent of an acid. The amino nitrogen atom is covalently bonded to the side group, and thus is a component of the polymer molecule. The tertiary nitrogen forms one bond with an intermediate group, preferably an aliphatic group, which is linked to the main chain of the polymer molecule. The two other covalent bonds of the nitrogen bear aliphatic groups, preferably low molecular weight alkyl groups with 1 to 4 C atoms.

Preferably the tertiary amino groups are a part of the monomer units of the polymer which monomer units are derived from acrylic or methacrylic monomers having the structure

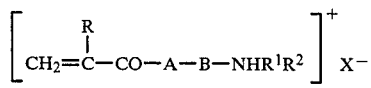

wherein

R is a hydrogen atom or a methyl group;
A is an oxygen atom or an $-NH-$ group; and
B is an aliphatic or arylaliphatic hydrocarbon group with 2-8 C atoms;
$R^1$ and $R^2$ are identical or different alkyl groups with 1-6 C atoms, or cycloalkyl groups; or are combined to form a single alkylene group which may be interrupted by an oxygen atom or an NH group; and
$X^-$ is a monovalent acid anion or one equivalent of a multivalent acid anion.

A preferred embodiment of the compound is an ester (where A is oxygen). B is preferably an alkylene group, possible branched, with at least 2 C atoms in a straight chain disposed between the amino nitrogen atom and the group A. Examples of monomers which upon salt formation become monomers with the described structure include dimethylaminoethyl acrylate, dimethylaminoethyl methacrylate, 2-dimethylaminopropyl acrylate, 2-dimethylaminopropyl methacrylate, piperidinoethyl acrylate, piperidinoethyl methacrylate, morpholinoethyl acrylate, morpholinoethyl methacrylate, dimethylaminobenzyl acrylate, dimethylaminobenzyl methacrylate, (3-dimethylamino-2,2-dimethyl)propyl acrylate, (3-dimethylamino-2,2-dimethyl)propyl methacrylate, (3-diethylamino-2,2-dimethyl)propyl acrylate, (3-diethylamino-2,2-dimethyl)propyl methacrylate, N-dimethylaminopropyl acrylamide, N-dimethylaminopropyl methacrylamide, N-(3-dimethylamino-2,2-dimethyl)-propyl acrylamide, N-(3-dimethylamino-2,2-dimethyl)propyl methacrylamide, N-(3-morpholino)propyl acrylamide, and N-(3-morpholino)propyl methacrylamide.

With inorganic or organic acids the above-described monomers containing tertiary amino groups are converted to the corresponding tertiary ammonium salts. Suitable acids include mineral acids such as hydrochloric, sulfuric acid, and phosphoric acid, as well as acid salts of polybasic acids such as sodium bisulfate and sodium dihydrogen phosphate. Examples of suitable organic acids include acetic acid and citric acid. The acids must be physiologically tolerable, since they tend to be liberated in the acid medium of the stomach. The amount of acid need not stoichiometrically correspond to the amount of the tertiary amino groups; a fraction of these groups may be in the base form. Further, an excess of acid may be employed. In this way a pH may be established at which the adjuvants such as pigments, softening agents, and the like have optimal stability, and at which the coating medium can be expected to be as compatible as possible with the medicine itself.

The amount of quaternized ammonium salt groups in the polymer must be sufficient to render the polymer soluble in the liquid component of the coating medium. However, the solubility of the polymer is not determined by these groups alone. If the polymer also contains a substantial amount of highly hydrophilic monomer units such as hydroxyalkyl esters of acrylic or methacrylic acid, these units contribute to its solubility in water and in aqueous solvent mixtures. The greater the proportion of organic solvents in the said liquid component, the smaller the content of tertiary amino groups and other hydrophilic moieties needs to be in order to render the polymer soluble. In the absence of carboxylamide or hydroxyl groups, water solubility is achieved at a proportion of at least 10 mole %, preferably 15 to 60 mole %, of monomer units with tertiary ammonium salts groups such as the acrylic and/or methacrylic monomers represented by the formula supra. If the proportion of monomer units having a tertiary amino or ammonium nitrogen atom in the side chain is greater than 20 mole %, it is sufficient if only a fraction of these groups, e.g. more than 10 mole % in the polymer as a whole is present in the ammonium salt form.

Other acrylic or methacrylic monomers typically employed as constituents in preparing the polymer are the alkyl esters of acrylic and/or methacrylic acid, particularly the lower alkyl esters with 1 to 4 C atoms in the alkyl group, as well as acrylamide and methacrylamide, and the already-mentioned hydroxyalkyl esters, which as a rule contain 2 to 4 C atoms in the hydroxyalkyl group. The alkyl esters are preferred; and among them methyl acrylate, ethyl acrylate, and n-butyl acrylate are particularly preferred.

To the extent possible, the hydrophilicity of the binder should not be greater than required for rendering the polymeric binder soluble in the liquid component. If, when the polymer is produced, a larger proportion of hydrophilic groups is incorporated in it than necessary to achieve solubility, the resulting coating may be hygroscopic to the extent that under high humidity conditions it becomes sticky. One of the advantages of the present invention is that when the hydrophilicity is adjusted to just the degree necessary for solubility, this inordinate degree of hygroscopicity is not attained.

Another important characteristic, in addition to hydrophilicity, is the hardness of the binder. In order to confer on the coating the desired elasticity and abrasion resistance, the binder should not be excessively hard. A tensile strength $\sigma_R > 10$ N,/mm² (where N is Newtons force), and an elongation at rupture $\epsilon_R > 250\%$ (measured according to DIN 53 455) are desired. Generally, a polymer comprised solely of the above-described monomer units with tertiary amino side groups yields a relatively hard binder upon drying. This hardness can be reduced by employing a sufficient proportion of soft comonomers, particularly lower molecular weight esters of acrylic acid. Also concurrently, softening agents may be added to the binder to achieve the same end.

The polymer may be prepared by radical polymerization of the monomers in water solution or aqueous alcohol solution. Preferably, a non-neutralized polymer is first prepared using the starting monomers in base form rather than with ammonium salt groups. Radical polymerization processes which have been known for a long time are available for polymerization of the monomers. For example, polymerization in organic solvents, and polymerization without a solvent. Since the polymer in the base form is relatively water-insoluble, another polymerization technique is emulsion polymerization in an aqueous phase. A powdered product may be produced from the organic polymer solutions or aqueous polymer dispersions by e.g., spray drying. Polymers produced without employing a solvent may be melted in an extruder and extruded to produce a fine granulate.

The molecular weight of the polymer affects the viscosity of the coating medium, which is also a function of the concentration of the polymer in the liquid component. Preferably, the molecular weight is between 50,000 and 250,000. The viscosity of the solution of the polymer in the liquid component in the absence of pigments and fillers should not be more than 100 mPa-sec, and preferably is about 20 to 50 mPa-sec, with the polymer content at least 5 wt. % of this solution.

Preparation of the Coating Medium

The elasticity and hardness of the pharmaceutical formulation coating depend on the ratio of pigment to binder and on the hardness of the binder itself. Thus, in choosing the binder one must take into account the intended pigment concentration.

In practice it is advantageous to prepare the liquid coating medium from the base-form of the polymer. The polymer as a medium-fine to fine powder or as a granulate is dissolved in the liquid component under agitation and with the addition of an acid. Preferably, cold water is employed. It is particularly advantageous to employ polymer powders which are suitable for use in the non-neutralized state in producing pharmaceutical formulation coatings from organic solutions. Such coating solutions have been known for decades.

The salt form which is eventually generated has a hardness greater than that of the starting polymer in base form. Starting with the base form, neutralizing with hydrochloric, citric, or phosphoric acid, and adding 20 wt. % of a softener, binders are obtained which show the following differences in the temperature at which the logarithmic damping decrement passes through a minimum in the torsional brail test ($T_{\lambda max}$ according to DIN 53 455). $T_{80}$ max is a measure of the hardness of the binder:

| Chloride form | $T_{\lambda max} = 86°$ C. |
| Citrate form | $T_{\lambda max} = 59°$ C. |
| Phosphate form | $T_{\lambda max} = 54°$ C. |

By addition of, e.g., 10 to 20 wt. %, based on the weight of the polymer, of a softening agent, the hardness of the binder can be lowered to a suitable value for use. Suitable softening agents are liquids which are soluble in water to at least a limited degree, (preferably at last 0.2% b.w. at 20° C.) are compatible with the polymer, and under the conditions of the coating process are nonvolatile or not very volatile. A criterion of compatibility is that upon drying, a clear film can be produced from the unpigmented binder and the softening agent, or that the binder dissolves in a larger amount of the softener. Suitable substances for use as softening agents generally have molecular weights between 200 and 20,000 and contain one or more hydrophilic groups in the molecule, e.g. hydroxyl, ether, or amino groups. Examples of suitable softening agents include citric acid alkyl esters, glyceryl triacetate, and polyethylene glycols of molecular weight 500 to 20,000.

In addition to the polymer containing the ammonium side groups, other binders may be dissolved in the present coating medium, which other binders are not suitable for use as a sole binder. Examples include polyvinyl alcohol, polyvinyl pyrrolidone, and polyethylene glycols.

A particularly significant embodiment of the invention employs the polymer together with a film-forming binder which is dispersed in the aqueous phase rather than being dissolved. The particle sizes in the dispersion are between 0.1 and 1 micron. The dispersed particles must flow together to produce a coherent film under the conditions of the coating and drying process. Ger. Pat. No. 1,617,351 (Brit. Pat. No. 1,213,348) discloses pharmaceutical formulation coatings prepared from such film-forming aqueous dispersions of binders, which binders are insoluble over the entire physiological pH range. In order to liberate the active ingredients from their insoluble coating, a water-soluble or alkali-soluble substance is incorporated in the coating, which substance is dissolved in the gastrointestinal tract. The active ingredients are then liberated by means of the resulting pores. The water-soluble substances used for this purpose in the prior art, such as polyethylene glycols, polyvinyl pyrrolidones, polyvinyl alcohols, and starch, have the disadvantage that unless added in substantial amounts, they do not appreciably enhance permeability, whereas if added in higher amounts, i.e., adequate amounts to raise permeability to an acceptable level they lead to an abrupt excessive increase in permeability because of destruction of the film integrity, or to undesired swelling, and these changes are accompanied by loss of important film properties such as hardness, gloss, and abrasion resistance.

The present polymers having ammonium groups produce the surprising result that they increase the permeability of pharmaceutical formulation coatings comprised of dispersions of water-insoluble binders, which increase is proportional to the amount of said polymers added. Coatings comprised of 30% of the presently employed polymer binder and 70% of the said water-insoluble binders can have the permeability of a thin paper membrane without substantial sacrifices in mechanical properties. In this way, film coatings can be produced which have outstanding hardness and elasticity.

A preferred embodiment of the invention comprises the production of pharmaceutical formulation coatings from a fluid, water-based film-forming coating medium, the binder component of which comprises a mixture with the following composition:
(a) 1-49 wt. % of a polymer comprising side groups having ammonium salt moieties; and
(b) 99-51 wt. % of a film-forming, dispersed binder, which binder is not water-soluble in the physiological pH range i.e., in physiological environments, viz. the alimentary tract.

The above polymers designated "b" are present in the pharmacologically unobjectionable film-forming aqueous dispersions mentioned in Ger. Pat. No. 1,617,351, e.g., dispersions of polyvinyl esters, polyvinyl acetals, polyvinyl chloride, butadiene-styrene copolymers, and particularly polyacrylic acid esters. The latter are as a rule comprised of as much as >90 wt. % of preferably lower alkyl esters of acrylic and/or methacrylic acid.

The Coating Method

All types of solid pharmaceutical formulations can be coated by the present method including tablets, dragees, pills, granules, pellets, crystals of active ingredients, and capsules. Also, all commonly customary coating techniques may be employed including the pan coating ("drageeing") process and the fluidized bed coating ("drageeing") process. Likewise, the present coating media may be employed in simultaneous coating and production of granules from active ingredient powders, whereby granules are produced which can be pressure-molded to form matrix tablets or can be packed into capsules.

The amount of coating medium applied is calculated such that a coating 5-50 microns thick is produced on the pharmaceutical form. If desired, the coating may be built up in a plurality of layers applied separately, which layers may be of different compositions.

The particular formulation of the coating medium employed depends on the coating method used and the film properties desired. For example, a low viscosity suspension with a solids content of up to 20 wt. % and a viscosity less than 100 mPa-sec may be employed in spraying methods. Such a suspension may be sprayed onto the pharmaceutical formulation substrate in, e.g., a fluidized bed apparatus or in a rotating pan. For molding onto pharmaceutical forms in individual portions in a process similar to the classical granulation technique, coating media of relatively high viscosity and relatively high solids content may be employed.

Drying during the film-forming process is usually conducted using warm air at 40° to 80° C. In the preferred embodiment, wherein the liquid component is exclusively comprised of water with the inventive soluble binder dissolved in it, the outlet air can be exhausted directly to the atmosphere without posing an environmental hazard. After the desired amount of coating medium is applied to the substrate, it is recommended that the film be dried in a warm air cabinet for a few hours, or in a stream of warm air at 40°-60° C. Appropriate formulations will yield coated pharmaceutical forms with a pleasant appearance, high gloss, high abrasion resistance, and good storage properties even in tropical climates.

Characteristics Relating to Liberation of the Coated Material in the Coated Pharmaceutical Formulations If the polymer having the ammonium salt groups is employed as the sole binder or in a mixture with other water-soluble binders, the result is pharmaceutical formulations having a readily water-soluble coating film, which film dissolves within several minutes in the physiological pH range of about 1 to 8 which exists in the digestive tract, and the active ingredients contained are liberated immediately. This liberation in the stomach is not dependent on food absorption or on the existence of any pathological states, and is as rapid when the stomach is operatively distended as when it is operatively contracted. Even if the pharmaceutical formulations passes very rapidly into the digestive tract, it is dissolved quickly in the digestive tract at pH 5-8. At the same time, the speed of dissolution can be made slow enough that the taste of the interior of the coated preparation is not detected when the formulation is swallowed, while on the other hand, when sucked-on in the mouth for a relatively long time, the coating dissolves, so that the coating is suitable for sublingual tablets.

When the said polymer is used in combination with non-water-soluble coating medium dispersions, any point within the entire range of immediately disintegrating to true delayed-release preparates may be achieved, with the speed of liberation being practically independent of the pH of the surrounding medium. In particular the combination of water dispersions of neutral polyacrylic and polymethacrylic ester polymers with the present polymers of acrylic and methacrylic monomers is distinguished by good physiological tolerability. Thus, when using such combinations, one can produce a variable system of coating formulations with different gradations of permeability, which system is well adjustable to the permeation properties and therapeutic requirements of the various active ingredients encountered.

Having generally described this invention, a further understanding can be obtained by reference to certain specific examples which are provided herein for purposes of illustration only and are not intended to be limiting unless otherwise specified.

EXAMPLE 1

A polymer was produced by radical polymerization without solvent from 50 wt. parts dimethylaminoethyl methacrylate, 25 wt. parts methyl methacrylate, and 25 wt. parts n-butyl methacrylate. The polymer was extruded at 140° C. with degassing, the identical-particle granulate was comminuted, and the gross fraction over 0.25 mm was removed by seiving.

1600 g of the polymer powder having 5.1 mol amino groups was suspended in 8.6 kg water, and 540 g=2.6 mol citric acid monohydrate ($C_6H_5O_7 \cdot H_2O$, m.w. 210.14) (representing 7.7 equivalents of carboxyl groups) was stirred in. The mixture was stirred vigorously, in addition, to ensure that the polymer particles did not agglomerate or stick to the walls. After about 2 hrs. of stirring, a slightly turbid, yellowish solution resulted, with a pH of 3.25. When poured into a layer about 100 micron thick and dried at room temperature, this gave a clear, non-sticky, brittle film. To 224 g of the said solution with 20% polymer content, on a dry weight basis there was added a solution of 3.4 g polyethylene glycol 6000 in 30 g water, as a softening agent, and 15 g talcum powder, as a lubricant. The resulting mixture was sprayed over 3 kg of tablets, each tablet weighing 140 mg and having the dimensions 7 mm diameter and 3.5 mm height, in a rotary coating vessel of diameter 35 mm rotating at 40 rpm, using a compressed air spray pistol with a 1 mm diameter nozzle and a spraying pressure of 0.6 bar The spraying process took 45 min, and the coated tablets were concurrently dried during the spraying via continuously blown-in warm air, said air having temperature about 70° C. The result was a smooth film coating having a mat finish, which film dissolved quickly in water or in synthetic gastric juices. In either medium, the coated tablets disintegrated in less than 2 min.

EXAMPLE 2

224 g of the 20 wt. % solution of the polymeric salt in citric acid, which solution was described in Example 1, was mixed with a solution of 3.4 g polyethylene glycol 6000 in 30 g water and with 200 g of a 30 wt. % pigment suspension having the following composition:

| | |
|---|---|
| Talcum powder | 32 g |
| Titanium dioxide | 12 g |
| Red lake | 12 g |
| Polyethylene glycol 6000 | 4 g |
| Water | 140 g |
| Total | 200 g |

Similarly to Example 1, the mixture was applied to a total of 3 kg of tablets of the size of those in Example 1, and under the same spraying conditions except that the total spraying time was 75 min. The result was uniformly colored film dragees having a mat finish, which dragees disintegrated within 2 min in water or synthetic gastric juices, with the speed of disintegration being the same in either medium.

EXAMPLE 3

100 g of a polymer prepared according to the procedure of Example 1, corresponding to 0.32 mol of amino groups, and having a particle size less than 0.25 mm, was suspended in 419 g water. 480 g of a 1 M aqueous solution of sodium dihydrogen phosphate, corresponding to 0.96 equivalents acid, was added under stirring. After a stirring time of 2 hr, a clear, yellowish solution resulted.

To 335 g of the said solution (17.5% solution on a dry weight basis) was added a solution of 3.4 g polyethylene glycol in 30 g water, and the resulting solution was mixed with 200 g of the pigment suspension described in Example 2.

When the resulting mixture was sprayed onto 3 kg of tablets analogously to Example 2, the result was relatively smooth and slightly glossy film-dragees which in water or synthetic gastric juices completely disintegrated within 2 min.

EXAMPLE 4

A polymer dispersion was produced by emulsion polymerization of 50 wt. parts (3-dimethylamino-2,2-dimethyl)propyl methacrylate and 50 wt. parts methyl methacrylate, in water, with 3 wt. % polyoxyethylene (20) sorbitan monoleate (trade name "Tween 80") and 0.1 wt. % sodium dodecyl sulfate as emulsifiers, and with a peroxide initiator. A powder was produced from this dispersion by spraying drying.

50 g of this powder, containing 0.125 mol amino groups, was suspended in 250 g water. 13 g citric acid monohydrate, corresponding to 0.186 equivalents of carboxyl groups, was added with stirring. After 3 hr of stirring, a light yellow, turbid solution resulted. After filtration there was obtained 310 g of a nearly clear solution with about 20 wt. % solids. The solution can be used further as described in Example 2.

EXAMPLE 5

167.5 g of a solution as described in Example 3, containing 17.5 wt. % of a polymer salt on a dry basis, formed with sodium dihydrogen phosphate, was mixed with 112 g of an emulsion polymerizate, i.e., an emulsion comprising the final reaction mixture containing a polymer prepared by the emulsion polymerization of neutral acrylate and methacrylate esters in amounts of 70 wt. % ethyl acrylate and 30 wt. % methyl methacrylate said emulsion containing 30 wt. % content of the polymer on a dry basis. The resulting mixture was diluted with 95 g water. After addition of 15 g talcum powder, the mixture was sprayed onto a total of 3 kg of tablets of 7 mm diameter, in a rotary coating vessel, over a period of 50 min. The tendency to stickiness, which is a significant problem when the neutral emulsion polymerizate is used alone, was not observed during the application process. The disintegration time in water of the finished coated tablets was less than 2 min.

EXAMPLE 6

600 g of an extruded copolymer produced from equal parts by weight of dimethylaminoethyl methacrylate and methyl methacrylate was stirred into 3.6 liters water, and 301 g sodium dihydrogen phosphate dihydrate was added. The granular particles of the extruded copolymer, with particle size of 1-2 mm, dissolved completely within 72 hr at room temperature. Water was added for dilution to make up 6000 g. 135 g of this solution, which contained 13.5 g of the copolymer (base form), was mixed with 405 g of an emulsion polymerizate, an i.e., an emulsion comprising the final reaction mixture of 30 wt. % (121.5g) polymer prepared by emulsion copolymerizing equal parts by weight of methyl methacrylate and ethyl acrylate. The ratio of the base-form of the copolymer to neutral (methyl methacrylate ethyl acrylate) copolymer was 1:9 by weight.

In addition, 200 g of a 15 wt. % pigment suspension with the following composition was added:

| | |
|---|---|
| Talcum powder | 8 g |
| Magnesium stearate | 10 g |
| Titanium dioxide | 4 g |
| Yellow lake E 102 | 5 g |
| Polyethylene glycol 6000 | 3 g |
| Water | 170 g |
| Total | 200 g |

This pigmented lake mixture was then sprayed onto a total of 1.5 kg of chlorpheniramine (Chlorphenamin) maleate pellets with a particle size range of 0.5-1.2 mm and an active ingredient content of 8 wt. %, in a laboratory fluidized bed apparatus (Uni-Glatt). Warm air at 40° C. was blown into the apparatus from below, and the spray nozzle (bore 1 mm diameter), which extended into the fluidized bed from above, was driven with compressed air at 1–2 bar. The spray coating process was carried out for 65 min. In synthetic digestive tract juices, the coated pellets liberated the active ingredient in delayed-release fashion. About 80% of the active ingredient was released within 6 hr.

EXAMPLE 7

In the formulation according to Example 6, 270 g of the solution of the base-form copolymer (containing 27 g polymer on a dry basis) was mixed with 360 g of an emulsion polymerizate containing 30 wt. % (108 g) of a polymer on a dry basis produced from monomers comprising equal parts by weight of methyl methacrylate and ethyl acrylate, wherewith the ratio of the basic copolymer to the neutral copolymer was 2:8 by weight. The resulting mixture was mixed with the above-described pigment suspension (Example 6), and the resulting mixture was used to coat chlorpheniramine maleate pellets analogously to Example 6. The result was an acceleration of the release of the active ingredient, with about 80% of the active ingredient being released within 4 hr.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A method for coating solid pharmaceutical formulations, comprising coating said solid formulation with an aqueous fluid, film-forming coating medium, the liquid component of which medium is comprised primarily of water, said method further comprising drying of the film: characterized in that a coating medium is employed the binder of which consists essentially of:
   (a) a polymer dissolved in the liquid component, which polymer is comprised of acrylic and/or methacrylic monomers, and is further comprised of side groups having a tertiary ammonium salt group, the nitrogen atom of which is covalently bonded to the side group, said polymer comprised of a homo- or copolymer of monomers of structure

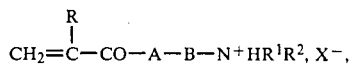

wherein
   R is a hydrogen atom or a methyl group;
   A is an oxygen or an —NH— group;
   B is an aliphatic or araliphatic hydrocarbon group with 2–8 C atoms;
   $R^1$ and $R^2$ are identical or different alkyl groups with 1–6 C atoms, or alicyclic groups, or together form an alkyl chain which may be broken by an oxygen atom or by an —NH— group; and
   $X^-$ represents monovalent acid anion or one equivalent of a polyvalent acid anion; and
   (b) a dispersed film-forming binder which is insoluble in the coating medium and which comprises the preponderant part of the total binder content of the coating medium.

2. A method according to claim 1; characterized in that a coating medium is employed wherein the aforementioned polymer (a) is comprised in the amount of 10–60 mol % of monomer units with a tertiary ammonium nitrogen atom, and in the amount of 90–40 mol % of monomer units comprised of alkyl esters of acrylic and/or methacrylic acid.

3. A method according to claim 1; characterized in that a coating medium is employed wherein the aforementioned polymer (a) additionally contains monomer units with a non-acid-neutralized tertiary amino nitrogen atom.

4. A method according to claim 1; characterized in that a coating medium is employed which contains a softening agent which is at least slightly soluble in water and is compatible with polymer (a).

5. A method according to claim 1; characterized in that a coating medium is employed which contains polymer (a) in the amount of 1–49 wt. % and binder (b) in the amount of 99–51 wt. %.

6. A method according to claim 1; characterized in that a coating medium is employed wherein the dispersed binder (b) is a polyacrylate ester containing units of alkyl esters of acrylic and/or methacrylic acid, said units being present in the amount of >90 wt. %.

7. A method according to claim 1; characterized in that the coating medium is sprayed onto the solid pharmaceutical formulation to be coated.

* * * * *